(12) United States Patent
Di Capua

(10) Patent No.: US 11,607,266 B2
(45) Date of Patent: Mar. 21, 2023

(54) ELECTROSURGICAL DEVICE

(71) Applicant: KYLIX S.R.L., Naples (IT)

(72) Inventor: Giulia Di Capua, Naples (IT)

(73) Assignee: KYLIX S.R.L., Naples (IT)

( * ) Notice: Subject to any disclaimer, the term of this patent is extended or adjusted under 35 U.S.C. 154(b) by 514 days.

(21) Appl. No.: 16/336,579

(22) PCT Filed: Sep. 26, 2017

(86) PCT No.: PCT/IB2017/055818
§ 371 (c)(1),
(2) Date: Mar. 26, 2019

(87) PCT Pub. No.: WO2018/055593
PCT Pub. Date: Mar. 29, 2018

(65) Prior Publication Data
US 2019/0231415 A1    Aug. 1, 2019

(30) Foreign Application Priority Data

Sep. 26, 2016  (IT) .......................... 102016000096420

(51) Int. Cl.
*A61B 18/14* (2006.01)
*A61B 18/00* (2006.01)
*A61B 18/12* (2006.01)

(52) U.S. Cl.
CPC ...... *A61B 18/1402* (2013.01); *A61B 18/1482* (2013.01); *A61B 2018/00577* (2013.01);
(Continued)

(58) Field of Classification Search
CPC ............ A61B 18/1402; A61B 18/1482; A61B 2018/00577; A61B 2018/126;
(Continued)

(56) References Cited

U.S. PATENT DOCUMENTS 5,413,575 A * 5/1995 Haenggi ............ A61B 18/1402
606/39
7,811,282 B2 * 10/2010 McClurken ............ A61B 18/12
606/49

(Continued)

FOREIGN PATENT DOCUMENTS

EP    1263341 B1    12/2002
EP    1435867 B1    7/2004
(Continued)

*Primary Examiner* — Khadijeh A Vahdat
(74) *Attorney, Agent, or Firm* — David B. Tingery; Bryant J. Keller; Kirton McConkie

(57) ABSTRACT

The electrosurgical device comprises at least one hollow body of elongated shape and having: a gripping portion, in turn, comprising a proximal ending part connectable to a current generator and to feeding means of an electro-conductive fluid; a contact portion comprising a distal ending part having one active electrode and one neutral electrode adapted to come into contact with the body of a patient; and at least one tubular duct passing through the hollow body and having one feeding hole of the fluid formed on the proximal ending part, and one delivery hole of the fluid formed on the distal ending part; the delivery hole is at least partially circular and extends around at least one of the electrodes.

10 Claims, 4 Drawing Sheets

(52) U.S. Cl.
CPC . *A61B 2018/126* (2013.01); *A61B 2018/1472* (2013.01); *A61B 2217/005* (2013.01); *A61B 2217/007* (2013.01); *A61B 2218/002* (2013.01); *A61B 2218/007* (2013.01)

(58) Field of Classification Search
CPC ...... A61B 2018/1472; A61B 2217/005; A61B 2217/007; A61B 2218/002; A61B 2218/007; A61B 18/14; A61B 2018/007
USPC .................................................... 606/21–50
See application file for complete search history.

(56) References Cited

U.S. PATENT DOCUMENTS

| | | |
|---|---|---|
| 2005/0043728 A1 | 2/2005 | Ciarrocca |
| 2005/0245923 A1* | 11/2005 | Christopherson .. A61B 18/1477 606/41 |
| 2007/0173760 A1* | 7/2007 | Fedenia ................ A61M 1/741 604/131 |
| 2013/0197506 A1 | 8/2013 | Evans et al. |
| 2014/0066929 A1* | 3/2014 | Mark ................. A61B 18/1482 606/50 |
| 2015/0157386 A1 | 6/2015 | Bloom et al. |

FOREIGN PATENT DOCUMENTS

| | | |
|---|---|---|
| EP | 1487365 B1 | 12/2004 |
| EP | 1827275 B1 | 9/2007 |
| EP | 1946716 A1 | 7/2008 |
| EP | 2011446 A2 | 1/2009 |
| EP | 1318758 B1 | 4/2009 |
| EP | 2129313 B1 | 12/2009 |
| EP | 2275050 A1 | 1/2011 |
| EP | 2305160 A1 | 4/2011 |
| ES | 2419159 A2 | 8/2013 |
| WO | WO-2013038042 A1 * | 3/2013 ......... A61B 18/1402 |

* cited by examiner

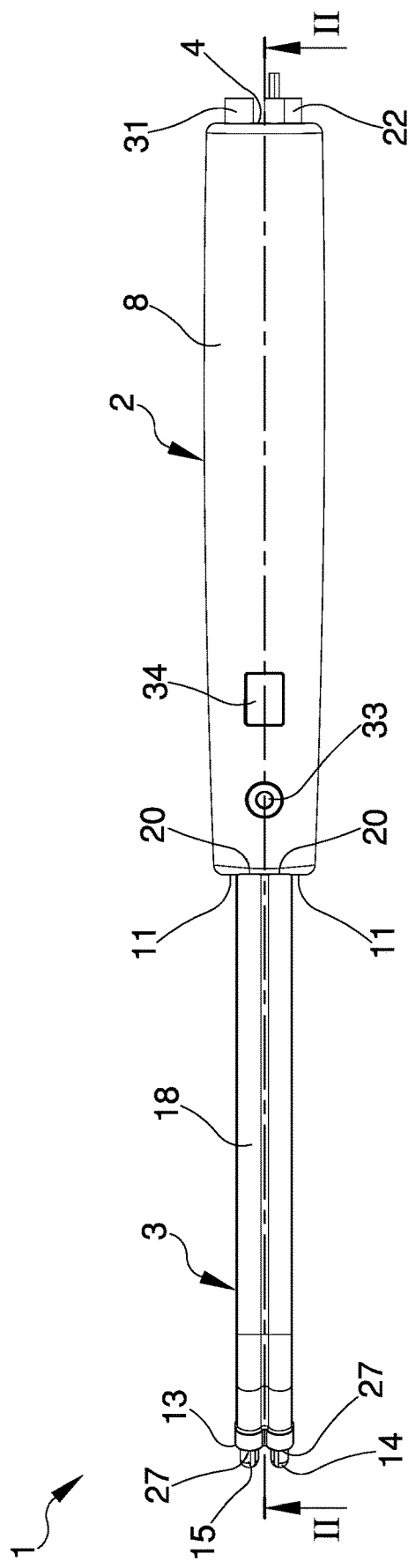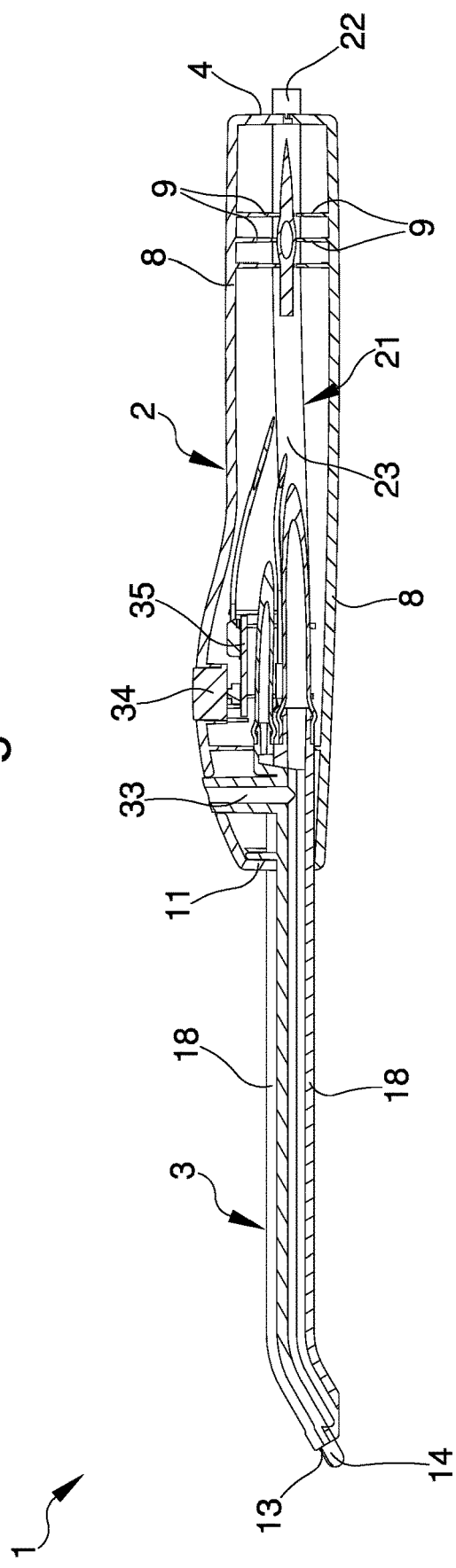

ELECTROSURGICAL DEVICE

TECHNICAL FIELD

The present invention relates to an electrosurgical device.

PRIOR ART

In medical practice, the use has been known for over a hundred years of devices adapted to apply an electrical charge, or alternatively high frequency waves, onto a patient's body.

The thermal effect caused by the application of such electrical charge causes a transformation of the cells of the affected tissue, resulting in its being cut and/or cauterized.

The use of such devices is widely employed to access the operating site, especially if the latter is obstructed by the presence of soft tissues, in order to prevent the formation of bleeding and to keep the operating site clean.

In fact, the presence of bleeding, tissue dissections, or of altered coagulation parameters, or patients with congenital or hemorrhagic disorders, makes the control of intra-operative conditions difficult to implement and involves a high risk for patient safety.

To date, the above devices are used in many medical fields such as ophthalmology, gynecology, cardiology, urology, neurology and oncology.

A first type of known device, the so-called Bovie pen, provides for heat application at a temperature greater than 100° C. by means of a dry electrode of pointed shape.

Such device has a number of drawbacks among which must be mentioned the fact that it causes drying of the tissues involved and the consequent adhesion of same to the electrode.

To the aforementioned drawback must be added the fact that the device causes perforation of the tissues involved, causing burns and leading to the formation of smoke.

To remedy at least partly some of these drawbacks, other types of electrosurgical devices have been designed.

Such known devices, which may be of the monopolar or bipolar type, generally have two electrodes, between which the electric charge occurs transmitted to the tissue to be cut.

Such devices comprise a gripping portion adapted to be gripped by an operator and having a first ending part connectable to a current generator and to feeding means for feeding an aqueous solution, and a second ending part associated with an elongated body.

The known electrosurgical devices also comprise on/off switching means for switching the current feeding means on and off which can be of the type of a pedal positioned underneath the operator's feet or of the type of a button element made on the gripping portion.

The extremal portion of the elongated body is provided with just one electrode, in the case of monopolar electrosurgical devices, or with two electrodes in the case of bipolar devices, and with at least an outlet hole for the aqueous solution which performs the function of a conductor.

The electrodes can have various shapes and dimensions depending on the application site and on the medical procedure wherein they are used; a first type of electrode has a substantially filiform shape and the latter is used to cut or cut out a tissue, a second type of electrode has a looped shape and is adapted to level the tissue, finally, a third type of electrode has a substantially spherical shape and is adapted to cauterize the tissue.

In the same way, the intensity, the frequency and the shape of the waves also varies according to the clinical application of the latter; in other words, the completely straightened and filtered waves produce a cut, the straight non-filtered waves determine the cut and the coagulation of the tissue involved, the partially straightened waves produce coagulation and electrocution, causing the surface destruction of the soft tissues.

Furthermore, the outlet hole of the aqueous solution is arranged at the side of the electrode, or electrodes, depending on whether the electrosurgical devices are monopolar or bipolar respectively.

In detail, the monopolar electrodes have an active electrode with small dimensions so as to facilitate the obtaining of a high-density current, and which is positioned on the extremal portion of the elongated body, and a neutral electrode with large dimensions, with a substantially planar conformation, positioned underneath the patient and adapted to collect the current coming out of the active electrode in such a way as to close the circuit.

Monopolar electrosurgical devices nevertheless have a number of drawbacks among which must be included the fact that the movement of the active electrode nearer to the patient's tissue produces a spark, which often causes burns and lesions.

Furthermore, the heat generated by the active electrode does not remain restricted in the tissue of interest, but spreads, causing lesions to the adjacent tissues.

To this must be added the fact that, in order to address the need to keep the surgical site clean, a suction device will have to be used which, because it has to be operated separately with respect to the monopolar electrosurgical device, requires the intervention of another operator, thus considerably complicating the use of the monopolar device itself.

To overcome the aforementioned drawbacks, at least in part, the above-mentioned bipolar electrosurgical devices have been made; the latter have both the active electrode and the neutral electrode positioned on the extremal portion of the elongated body.

In this mode, both electrodes are present on the surgical site and the current produced by the generator only crosses the portion of tissue between the two electrodes, without passing through the patient's body.

Furthermore, the extremal portion is provided with two outlet holes for the aqueous solution, arranged at the side of the two electrodes.

The aforementioned types of electrosurgical devices are described in patent documents EP1263341, EP1946716, EP1827275, EP2129313, EP1435867, EP2275050, EP1487365, EP2305160, EP1318758 and EP2011446.

However, even bipolar electrosurgical devices are not free of drawbacks.

In particular, the presence of organic residues on the operating field causes the obstruction of the aqueous solution outlet holes which, by occluding the electrodes, determines a rise in the intensity of the current with consequent formation of tissue lesions.

Furthermore, in the case of organs located in depth, the aqueous solution accumulates in the areas adjacent to the latter, and thus immediately requires being sucked up.

In the same way as the monopolar electrosurgical devices, the accumulated aqueous solution is sucked up by means of a suction device separated with respect to the electro surgical device itself which, because it requires the intervention of another operator, considerably complicates the performance of the medical operations.

Finally, with particular reference to liver surgery and to the parenchymal transaction procedure, the latter, to date, is performed by using a combination of instruments and techniques which usually comprise a dissection device of the type of a clamp, or of an ultrasonic dissector, and an instrument for achieving hemostasis of the type of a surgical suture, or a clip.

Nevertheless, such procedure has various drawbacks tied to the loss of intraoperative blood and the need for perioperative transfusions which considerably increase the risk of surgical mortality and morbidity, putting at risk the patient's long-term survival.

To this must be added that in the field of oncology, the absence of a single instrument aimed at fully completing the parenchymal transection procedure has determined an increase in the rate of cancer recurrence.

Consequently, in the last ten years, many techniques have been tested and developed aimed at reducing the loss of intraoperative blood to the utmost during such operation.

To overcome the above problems at least in part, the so-called Pringle maneuver is known which involves stopping bleeding during liver resection operations by means of the use of a clamp, or through the compression of the portal vein or hepatic artery.

Nevertheless, such method as well is not without drawbacks tied to the considerable invasiveness of the technique itself, often the cause of hemorrhages, and to which must be added the impossibility of carrying out the entire operation by means of a single device, thus considerably extending operation times.

In this respect, recent studies have shown how the loss of blood combined with the duration of the operation represent the main factors affecting the end result. It is easy to appreciate how there is a particularly strongly felt need to provide devices able to considerably reduce the invasiveness of the procedure, reducing bleeding and with it the need for blood transfusions, which leads to a considerable reduction in operation times.

DESCRIPTION OF THE INVENTION

The main aim of the present invention is to provide an electrosurgical device which permits achieving, by means of a single device, the coagulation, the transection and the hemostasis of the tissue involved.

One object of the present invention is to provide an electrosurgical device which permits considerably reducing the current intensity used compared to known devices, operating in deep tissues and in areas bordering on vital organs without the risk of causing burns and lesions to the tissues adjacent to the surgical site itself.

Another object of the present invention is to provide an electrosurgical device which permits avoiding the Pringle maneuver when used in liver surgery.

A further object of the present invention is to provide an electrosurgical device which permits keeping the operating field clean, eliminating the presence of blood.

Yet another object of the present invention is to provide an electrosurgical device which can be used in the case of any neoplastic localization, and any type of liver.

Finally, a further object of the present invention is to provide an electrosurgical device which allows overcoming the aforementioned drawbacks of the prior art within the scope of a simple, rational, easy, efficient to use and cost-effective solution.

The aforementioned objects are achieved by the present electrosurgical device, having the characteristics of claim 1.

BRIEF DESCRIPTION OF THE DRAWINGS

Other characteristics and advantages of the present invention will become more evident from the description of a preferred, but not exclusive, embodiment of an electrosurgical device, illustrated by way of an indicative, but non-limiting example, in the attached drawings in which:

FIG. 1 is a plan view from above of the device according to the invention;

FIG. 2 is a sectional view along the plane II of FIG. 1;

EMBODIMENTS OF THE INVENTION

Figure 3:
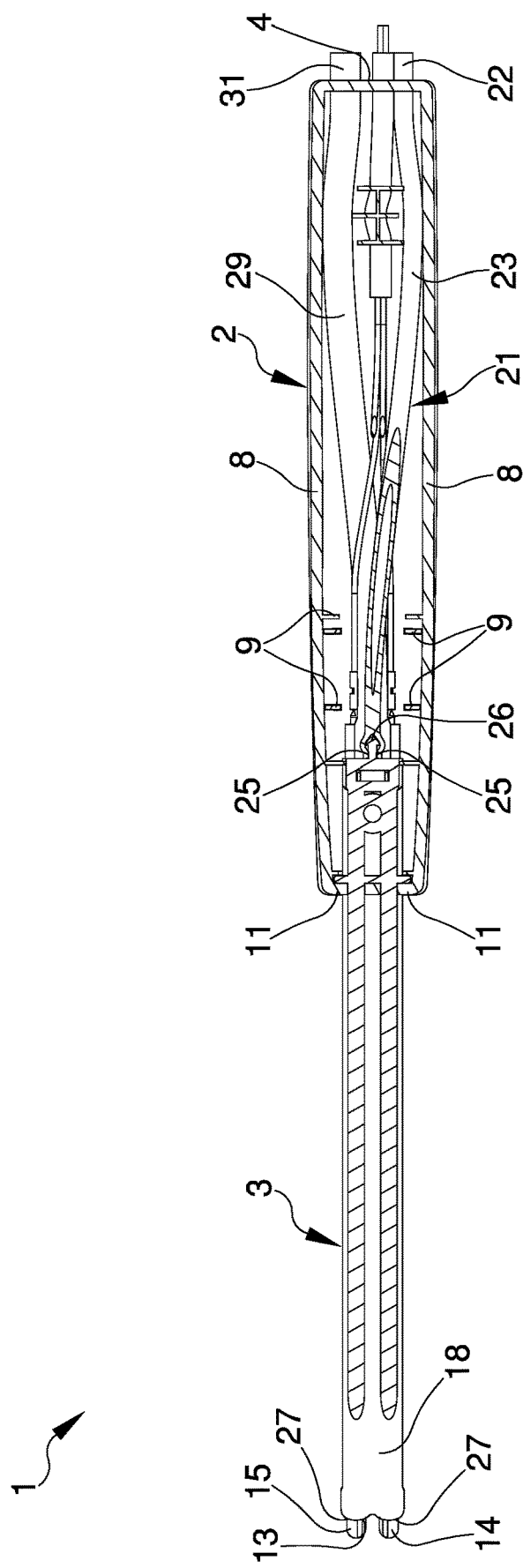
FIG. 3 is a sectional view from above of the device according to the invention.
Figure 4:
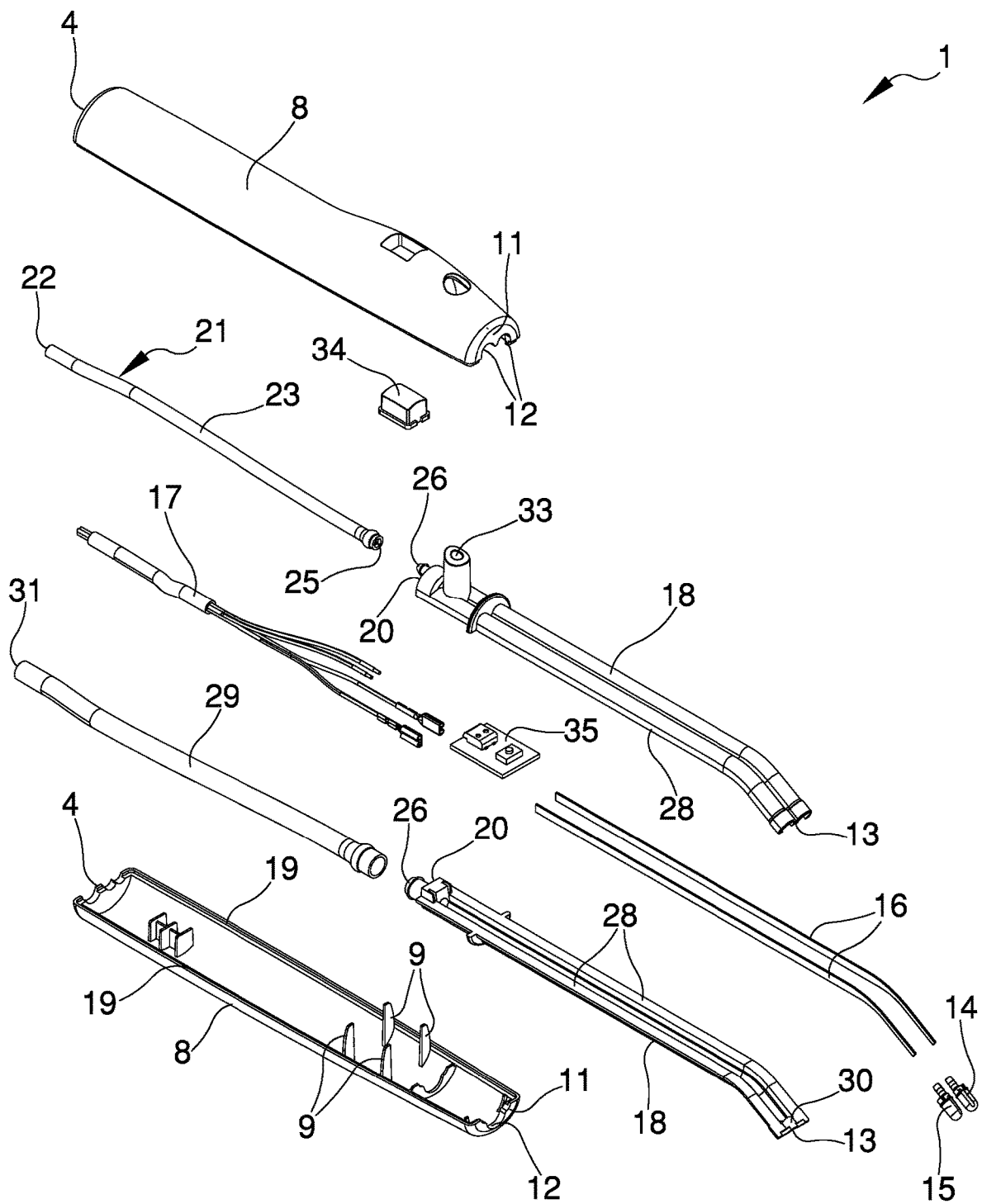
FIG. 4 is an exploded view of the device according to the invention.
Figure 5:
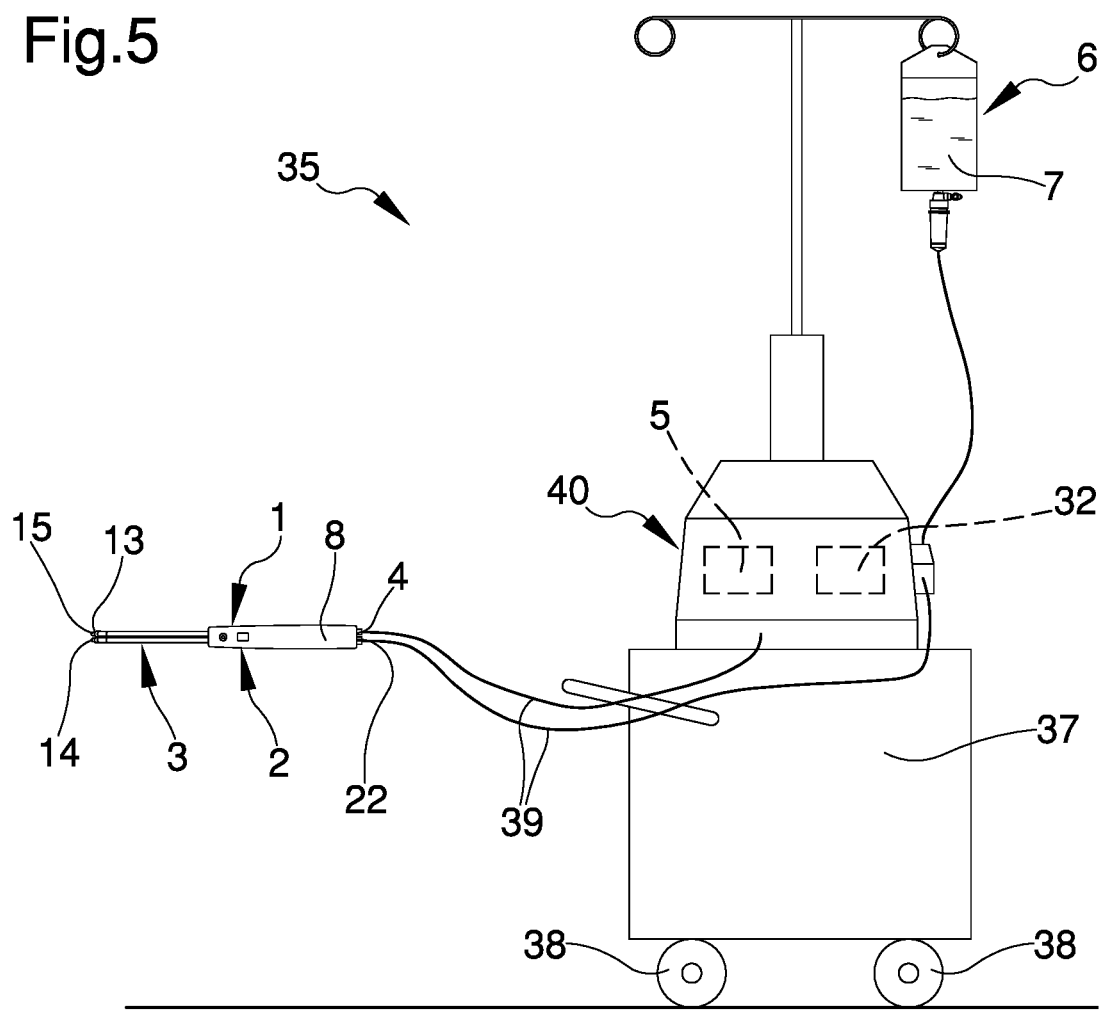
FIG. 5 is a schematic representation of the appliance according to the invention.
Figure 6:
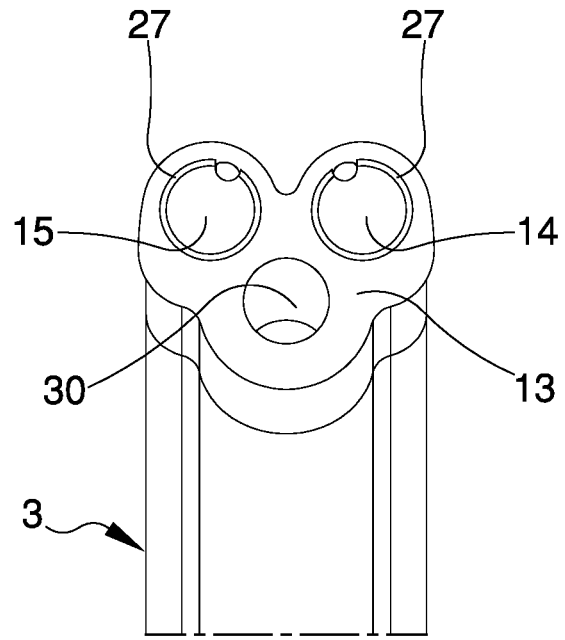
FIG. 6 is a sectional view of a detail of FIG. 1.

With particular reference to these illustrations, reference numeral 1 globally indicates an electrosurgical device.

The device 1 comprises one hollow body 2, 3 of elongated shape and having a gripping portion 2, in turn, comprising a proximal ending part 4 connectable to a current generator 5 and to feeding means 6 of an electro-conductive fluid 7.

It is useful to point out that in the present discussion the "distal" and "proximal" adjectives are considered with reference to the current generator 5 and to the feeding means 6.

Advantageously, the current generator 5 is adapted to generate a radio frequency current.

In detail, the radio frequency current has a power between 20 and 200 Watts. Preferably, the fluid 7 is of the type of a saline solution.

The gripping portion 2 has an ergonomic shape adapted to facilitate its gripping and handling by the operator.

Furthermore, the gripping portion 2 comprises two first half-shells 8 associable the one with the other by interposition of connection means 9 provided with a plurality of toothed elements made on both the first half-shells 8 and which, in an assembly configuration (FIGS. 1 and 2), are adapted to operate in conjunction with one another to associate by slotting into one another.

Each first half-shell 8 has a first slotting ending part 11 opposite the proximal ending part 4 and shaped in such a way as to define, in an assembly configuration, a housing seat 12.

Furthermore, the hollow body 2, 3 comprises a contact portion 3 having a distal ending part 13 provided with an active electrode 14 and with a neutral electrode 15 adapted to come into contact with the body of a patient.

With reference to the particular embodiment shown in the illustrations, the electrodes 14, 15 are substantially dome-shaped.

In particular, each electrode 14, 15 can be connected to the current generator 5 by means of a metal element 16 with elongated shape, in turn associated with power transmission means 17 of the type known to the expert in the sector.

In the same way as the gripping portion 2, the contact portion 3 also comprises two second half-shells 18 provided with joining edges 19 which, in an assembly configuration, are associated with one another by slotting.

The second half-shells 18 comprise a second slotting ending part 20, opposite the distal ending part 13 and provided with two connecting elements 26 with tubular shape and adapted to allow fluidic communication between the gripping portion 2 and the contact portion 3.

More in detail, the first and the second half-shells 18 can be made separately using forming techniques, such as injection molding, and subsequently assembled together or, alternatively, they can be made in a single body piece.

The hollow body 2, 3 comprises a tubular duct 21 passing through the hollow body itself and having one feeding hole 22 of the fluid 7 formed on the proximal ending part 4, and one delivery hole 27 of the fluid 7 formed on the distal ending part 13.

As can be seen in the illustrations, the tubular duct 21 comprises a first section 23 passing through the gripping portion 2.

In detail, the first section 23 comprises a first ending part 24 provided with the feeding hole 22, and a second ending part 25 opposite the first ending part 24 and adapted to house the respective connecting element 26; this allows the passage of the salt solution 7 from the first section 23 to the contact portion 3 and the consequent distribution of the flow to the respective delivery holes 27. The distribution of the flow of salt solution 7 is allowed by the shape of the contact portion 3.

In fact, with reference to the particular embodiment shown in the illustrations, the contact portion 3 is shaped to define, in an assembly configuration, two housing ducts 28 for containing the electrodes 14, 15 and the relative metal elements 16.

At the same time, the two housing ducts 28 allow for the passage of the salt solution 7; this means that the salt solution 7 flows, dropping by gravity, inside the two housing ducts 28.

According to the invention, the delivery hole 27 is at least partially circular and extends around at least one of the electrodes 14, 15.

In detail, the delivery hole 27 has a substantially annular shape surrounding at least one of the electrodes 14, 15.

With reference to the particular embodiment shown in the illustrations, the tubular duct 21 comprises two delivery holes 27 respectively surrounding each of the electrodes 14, 15.

In particular, the tubular duct 21 has at least one section coaxial to each of the electrodes 14, 15.

It is well to underline that the annular shape of the delivery holes 27 permits skimming each of the electrodes 14, 15, by wetting them uniformly.

More in detail, each electrode 14, 15 extends overhanging with respect to the distal ending part 13 and the delivery holes 27 are made in a receding position with respect to the top of the electrodes themselves; this enables the salt solution 7 to come out and run along the entire surface of the electrodes 14, 15.

Moreover, the device 1 comprises a suction duct 29 for suctioning the biological residues which passes through the hollow body 2, 3.

In particular, the suction duct 29 comprises a suction mouth 30 of the biological residues which is formed on the distal ending part 13 and an exhaust mouth 31 of the biological residues which is formed on the proximal ending part 4 and connectable to the suction means 32.

The device 1 comprises control means 33 of the suction means 32 which are formed on the gripping portion 2.

With reference to the particular embodiment shown in the illustrations, the control means 33 are of the type of a through hole which is formed on the gripping portion 2.

The suction force varies according to the operator's needs; this means that the operator, by blocking the through hole 33 at least partially with his/her finger, increases the suction force generated by the suction means 32 and, vice versa, by freeing the through hole 33, reduces the suction force.

The device 1 comprises on/off switching means 34, 35 of the power which are formed on the gripping portion 2.

The on/off switching means 34, 35 are of the type of a button element.

In particular, the button element 34, 35 comprises an activation surface 34 which can be pressed by the operator and a contact element 35 of the type known to the expert in the sector and adapted to transmit the on/off signal to the electrodes 14, 15.

Advantageously, the electrodes 14, 15 are arranged symmetrically with respect to the suction mouth 30.

The present invention also relates to an appliance 36 for electro-surgery.

The appliance 36 comprises a supporting frame 37 for resting on the ground provided with wheel elements 38 adapted to allow the displacement thereof in the surrounding environments.

Furthermore, the appliance 36 comprises a power supply and control unit 40 associated with the supporting frame 37 and provided with feeding means 6 of a radio frequency current and suction means 32 of biological fluids.

The appliance 36 comprises the device 1, and the latter is operatively connected to the power supply and control unit 40 by interposition of connecting means 39.

The operation of the present invention is as follows.

The operator turns on the appliance 36 and, by gripping the device 1, approaches the contact portion 3 to the operating site.

By pressing the activation surface 34, the contact element 35 drops and allows the flow of the radio frequency current to the electrodes 14, 15.

At the same time as the electrical charge applied to the patient's tissue and adapted to cause its cutting and healing, the salt solution 7 runs by gravity along the tubular duct 21 and the relative housing ducts 28, before then coming out of the respective delivery holes 27.

The salt solution 7, coming out of the delivery holes 27, wets the electrodes 14, 15 uniformly by skimming the entire surface of the latter.

The operator, by placing their finger on the through hole 33, adjusts the intensity of the suction force generated by the suction means 32.

In detail, the suction mouth 30 positioned inside the operating site ensures the removal of the biological residues therein and eliminates the risk of accumulation of the salt solution 7.

It has in practice been ascertained that the described invention achieves the intended objects.

The fact is underlined that the particular solution of providing annular delivery holes surrounding the electrodes, in combination with the presence of a suction mouth prevents the obstruction of the electrodes and permits using the device at lower electric powers with respect to known devices, and at the same time enables the maintaining of an operating site devoid of blood.

To this must be added the fact that the absence of accumulations of salt solution allows using the above device in deep tissues positioned close to vital organs, without the risk of any injury to these.

The invention claimed is:

1. An electrosurgical device, comprising at least onea hollow body of elongated shape and having:
    a gripping portion comprising a proximal ending part connectable to a current generator and to a feeding means of an electro-conductive fluid, wherein the current generator is adapted to generate a radio frequency current having a power between 20 and 200 Watts;

a contact portion comprising a distal ending part having an active electrode and a neutral electrode adapted to come into contact with a body of a patient; and
a tubular duct passing through said hollow body and having a feeding hole of said electro-conductive fluid formed at said proximal ending part;
wherein said tubular duct comprises:
a first delivery hole of said electro-conductive fluid, being formed at said distal ending part and substantially surrounding the neutral electrode; and
a second delivery hole of said electro-conductive fluid being formed at said distal ending part and substantially surrounding the active electrode,
wherein a distribution of a flow of said electro-conductive fluid is controlled by a shape of the contact portion,
wherein the electrosurgical device further comprises a suction duct for suctioning biological residue that passes through said hollow body, wherein said suction duct in use is disposed below the first delivery hole and the second delivery hole, said active electrode and said neutral electrode being arranged symmetrically with respect to a suction mouth of said suction duct and said active electrode and said neutral electrode each extend overhanging with respect to the distal ending part and the first and second delivery holes are made in a receding position with respect to a top of the active electrode and the neutral electrode, each of said active electrode and said neutral electrode extending longitudinally downwards over the suction duct to allow the electro-conductive fluid to run by gravity during use along the tubular duct and the first delivery hole and the second delivery hole, respectively, and coming out of the first delivery hole and the second delivery hole respectively to wet the active electrode and the neutral electrode uniformly by skimming an entire exposed surface of the active and the neutral electrodes that is exposed from the contact portion.

2. The device according to claim 1, wherein said tubular duct has a section coaxial to each of said active electrode and said neutral electrode.

3. The device according to claim 1, wherein said suction duct comprises the suction mouth formed at said distal ending part and an exhaust mouth for exhausting said biological residue, said exhaust mouth formed on said proximal ending part and connectable to a suction means.

4. The device according to claim 3, further comprising a control means of said suction means formed on said gripping portion.

5. The device according to claim 1, wherein said electro-conductive fluid comprises a saline solution.

6. The device according to claim 1, further comprising on/off switching means for power which are formed on said gripping portion.

7. An appliance for electro-surgery, comprising:
a supporting frame for resting on a ground surface;
a power supply and control unit associated with said supporting frame and, in turn, comprising:
a radio frequency current generator; and
a suction means of biological fluids;
wherein the appliance for electro-surgery comprises the electrosurgical device according to claim 1.

8. The appliance according to claim 7, wherein said electrosurgical device is operatively connected to said power supply and said control unit by interposition of connecting means.

9. An electrosurgical device, comprising:
a gripping portion comprising a proximal ending part connectable to a current generator and to a feeding means of an electro-conductive fluid, wherein said current generator is adapted to generate a radio frequency current having a power between 20 and 200 Watts;
a contact portion comprising a distal ending part having an active electrode and a neutral electrode adapted to come into contact with a body of a patient, the distal ending part having a three-lobed shape; and
a tubular duct extending through said electrosurgical device and having a feeding hole of said electro-conductive fluid formed at said proximal ending part, a first delivery hole surrounding at least a portion of said active electrode; and
a second delivery hole surrounding at least a portion of said neutral electrode,
wherein a distribution of a flow of said electro-conductive fluid is at least partially controlled by the three-lobed shape of said distal ending part of said contact portion,
wherein said electrosurgical device comprises a suction duct for suctioning biological residue that passes through said electrosurgical device, wherein said active electrode and said neutral electrode are arranged symmetrically, and are offset in position, with respect to a suction mouth of said suction duct, and
wherein a portion of said active electrode and a portion of said neutral electrode extends from and overhangs with respect to said distal ending part and said first and second delivery holes are made in a receding position with respect to a top of said active and neutral electrodes themselves, each of said active electrode and said neutral electrode extending longitudinally downwards over the suction duct,
wherein the gripping portion comprises an upper surface that is configured to contact a palm of a user's hand during use and a lower surface that is configured to contact a portion of a finger of the user's hand when the electrosurgical device is in use,
wherein a first portion of said contact portion extends from said gripping portion along a substantially straight line, and
wherein a distal end portion of said contact portion is bent down, along with a portion of the active electrode and a portion of the neutral electrode, with respect to said first portion of said contact portion, and
wherein the electrosurgical device is configured to allow the electro-conductive fluid to run in a use position by gravity along the tubular duct and to come out of the first and second delivery holes, respectively, and wet said active and said negative electrodes uniformly by skimming an entire exposed surface of said active electrode and said negative electrode.

10. The electrosurgical device of claim 9, wherein the gripping portion comprises an upper surface that is configured to contact a palm of a user's hand during use and a lower surface that is configured to contact a portion of a finger of the user's hand when the electrosurgical device is in use, and wherein said suction duct is disposed at least partially below said first delivery hole and said second delivery hole.

* * * * *